(12) United States Patent
Gellert et al.

(10) Patent No.: US 6,447,581 B2
(45) Date of Patent: Sep. 10, 2002

(54) GAS FLOW SWITCHING DEVICE

(75) Inventors: Udo Gellert, Bellheim; Friedhelm Mueller, Linkenheim-Hochstetten; Arno Steckenborn, Berlin, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/816,474

(22) Filed: Mar. 26, 2001

Related U.S. Application Data

(63) Continuation of application No. PCT/DE99/03054, filed on Sep. 23, 1999.

(30) Foreign Application Priority Data

Sep. 24, 1998 (DE) .......................................... 198 43 942

(51) Int. Cl.[7] .............................................. B01D 15/08
(52) U.S. Cl. .............................. 96/102; 96/105; 96/106
(58) Field of Search .................................. 96/101–106

(56) References Cited

U.S. PATENT DOCUMENTS

| | | | | |
|---|---|---|---|---|
| 3,150,517 A | * | 9/1964 | Kuffer et al. ............. 96/106 X |
| 4,394,263 A | | 7/1983 | Dosch et al. ............. 210/198.2 |
| 4,861,358 A | | 8/1989 | Mueller et al. ............ 55/386 |
| 5,641,400 A | | 6/1997 | Kaltenbach et al. ..... 210/198.2 |
| 5,720,798 A | | 2/1998 | Nickerson et al. ............ 96/102 |
| 5,792,943 A | | 8/1998 | Craig ......................... 73/23.22 |

FOREIGN PATENT DOCUMENTS

| | | | | |
|---|---|---|---|---|
| DE | 2806123 C2 | | 8/1979 | |
| DE | 2840612 | * | 3/1980 | .................. 96/104 |
| DE | 3735814 A1 | | 5/1989 | |
| EP | 0 003 617 A1 | | 8/1979 | |
| EP | 0 386 033 B1 | | 9/1990 | |
| EP | 0 789 238 A1 | | 8/1997 | |
| SU | 0873116 | * | 10/1981 | .................. 96/105 |

* cited by examiner

*Primary Examiner*—Robert H. Spitzer
(74) *Attorney, Agent, or Firm*—Sughrue Mion, PLLC

(57) ABSTRACT

To switch gas flows between gas sources and gas sinks, a gas flow switching device includes gas passages, which communicate with one another and which have connecting points for the gas sources and the gas sinks. Furthermore, the gas flow switching device has a device for setting different pressures. To simplify the construction of the gas flow switching device and to achieve precisely defined pressure and flow conditions without the need for calibration, the gas flow switching device has two plates (9, 10), which are positioned on top of one another and joined together. The two plates (9, 10) have congruent channels (11) on their respective sides that face one another. These channels (11) have semicircular cross sections and form gas passages (4 to 8). In addition, at their lateral exit points from the plates (9, 10), the channels (11) form connecting points (12 to 17).

12 Claims, 5 Drawing Sheets

GAS FLOW SWITCHING DEVICE

This is a Continuation of International Application PCT/DE99/03054, with an international filing date of Sep. 23, 1999, which was published under PCT Article 21(2) in German, and the disclosure of which is incorporated into this application by reference.

FIELD OF AND BACKGROUND OF THE INVENTION

The invention relates to a gas flow switching device for switching gas flows between gas sources and gas sinks. The gas flow switching device includes gas passages that communicate with one another and connecting points for the gas sources and gas sinks. Furthermore, the gas flow switching device includes a device for setting different pressures at predefined connecting points.

German Patent DE 28 06 123 C2 teaches a gas flow switching device that is used to change gas flow directions in a chromatographic separation column switching system. Therein, pressure drops of changing direction are generated between suitable points in the separation column switching system. To this end, the known gas flow switching device includes a main gas passage having two connecting points, which is disposed between two separation columns. In the vicinity of each of the two connecting points, the main gas passage is connected with a respective auxiliary gas passage via a respective connecting gas passage. The two auxiliary gas passages are connected with a carrier gas source via a device that comprises several valves for setting different pressures. By setting different pressure drops between the auxiliary gas passages themselves and between the auxiliary gas passages and the connecting points of the main gas passage, a gas sample exiting from the first separation column may enter the second column or may be prevented from entering the second column. Therein, the latter event occurs in the operating mode "cut." In this case, the gas sample is directed to a downstream detector or to a third separation column via the corresponding auxiliary gas passage. Furthermore, the first separation column with the carrier gas may be backflushed from the carrier gas source. The valves required for switching the gas flows come into contact with the carrier gas only but not with the gas sample. Moreover, the valves can be disposed outside the oven that is typically used to heat the separation columns.

For implementing the gas passages, the known gas flow switching device has a block with a center bore into which the end pieces of the two separation columns are inserted from both sides. The main gas passage includes a capillary, which extends coaxially in the center bore and whose ends project into the end pieces of the separation columns. The auxiliary gas passages are embodied as capillaries, which are inserted into the block and which lead into two spatial halves of the center bore. Therein, the spatial halves are sealed against one another. The connecting gas passages are formed by the annular gaps between the end pieces of the separation columns and by the capillary of the main gas passage that projects into the separation columns. The multipart construction of the known gas flow switching device is thus relatively complex. In addition, the parts of the known gas flow switching device must be calibrated in relation to one another.

European Patent EP 0 386 033 B1 teaches a further gas flow switching device, which is used for a valve-less metering of a gas sample for gas chromatographic analysis purposes. For this purpose, a carrier gas passage and a sample gas passage, which communicate with one another via a connecting gas passage, are connected to a carrier gas source via a device for setting different pressures. Therein, a metering device is disposed between the carrier gas source and the sample gas passage for injecting a sample gas slug into the carrier gas flow. The sample gas passage has the form of a tubular chamber. The carrier gas passage includes two interior tubes of different diameters, which penetrate the chamber and whose ends are pushed into one another so as to form an annular gap. This annular gap represents the connecting gas passage between the sample gas passage and the carrier gas passage. By adjusting different pressures in the carrier gas passage and in the sample gas passage, the sample gas from the sample gas passage is prevented from entering the carrier gas passage at the location of the annular gap. Alternatively, the sample gas from the sample gas passage may be specifically channeled into the carrier gas flow flowing through the carrier gas passage. In this known gas flow switching device too, the multipart construction is comparatively complex.

OBJECTS OF THE INVENTION

It is an object of the invention to simplify the construction of a gas flow switching device, wherein precisely defined pressure and flow conditions are to be achieved without the need for calibration.

SUMMARY OF THE INVENTION

This and other objects of the invention are achieved by a gas flow switching device for switching gas flows between gas sources and gas sinks. The gas flow switching device according to the invention includes two plates, which are positioned on top of one another and which are joined together. These plates have congruent channels on those sides of the two plates that face each other. The congruent channels have semicircular cross sections and form gas passages that communicate with each other. Furthermore, the congruent channels form connecting points for the gas sources and the gas sinks at points at which the congruent channels exit the two plates. In addition, the gas flow switching device according to the invention includes a device for setting different pressures at predefined ones of the connecting points.

The channels are produced in the plates with great technological precision. Therefore, the desired pressure and flow conditions, for which the geometries of the gas passages are calculated, can actually be obtained in practice. In contrast to the parts of the known gas flow switching devices, the plates of the gas flow switching device according to the present invention are comparatively easy to calibrate, and the joining of the plates is done automatically or semi-automatically. Finally, the planar structure of the gas flow switching device according to the invention is highly compact. Very small dimensions are obtained, particularly if the gas passages are produced micromechanically.

The gas sources and gas sinks are preferably connected with the gas passages of the gas flow switching device via capillaries. To this end, the cross sections of the channels at the connecting points are larger than the cross sections of the channels in the area of the gas passages in between the connecting points, and the capillaries, together with their ends, are inserted into the connecting points. Therein, the cross sections of the areas of the gas passages located directly behind the connecting points correspond to the inner cross sections of the capillaries to prevent the creation of flow impediments.

The channels in the plates may principally be made in various ways, e.g., by means of a laser. The plates are preferably made of monocrystalline silicon in which the channels are formed by isotropic etching. This is done, for instance, by means of a mixture of hydrofluoric acid and nitric acid. Alternatively, in the area of the channels, the monocrystalline silicon may be converted into porous silicon and subsequently removed by etching. The etching process in the porous silicon is isotropic, so that the channels formed therein have the desired semicircular cross sections. The channels may be lined with a silicon dioxide layer in order to protect them against the flowing gas.

To switch sample gas and carrier gas flows between two chromatographic separation columns, as it is known from the aforementioned German Patent DE 28 06 123 C2, the channels in the plates of the gas flow switching device according to the invention form a main gas passage, two auxiliary gas passages and two connecting gas passages. Moreover, a respective auxiliary gas passage extends on either side of the main gas passage. Each of the two auxiliary gas passages is connected to the main gas passage via one of the connecting gas passages. The junction points of the connecting gas passages to the main gas passage are mutually offset along the main gas passage. The cross sections of the connecting gas passages are smaller than the cross sections of the main gas passage and the cross sections of the auxiliary gas passages. The cross section of the main gas passage in the area between the junction points of the connecting gas passages is smaller than the cross section outside that area. In a generally known manner, the main gas passage is series-connected to the two separation columns between these columns, and the auxiliary gas passages on one side are connected to a carrier gas source via the device for setting different pressures. In order to measure the different pressures or pressure drops between the auxiliary gas passages, which are required for switching the gas flows between the separation columns, each of the auxiliary gas passages is advantageously connected to connecting points for pressure measuring devices via branching gas passages.

To meter a sample gas, particularly for gas chromatographic analysis purposes as disclosed in the German laid-open publication DE 37 35 814 A1, the channels in the plates of the gas flow switching device according to the invention form a carrier gas passage, a sample gas passage, as well as a connecting gas passage between the carrier gas passage and the sample gas passage. At the branch of the connecting gas passage from the sample gas passage, the cross section ratio of the connecting gas passage and the continuation of the sample gas passage corresponds to a predefined dividing ratio of the sample gas flow. In a generally known manner, the carrier gas passage and the sample gas passage are, on one side, connected to a carrier gas source via the device for setting different pressures. A metering unit for injecting a sample gas slug into the carrier gas flow is disposed between the carrier gas source and the sample gas passage. By determining the cross section of the connecting gas passage and the cross section of the continuation of the sample gas passage as a function of the adjusted division of the sample gas flow, discrimination between differently sized gas molecules is prevented when a portion of the sample gas is diverted from the sample gas passage into the connecting gas passage. Large molecules, e.g., molecules of the sample gas, are not as easily deflected as smaller molecules, e.g., molecules of the carrier gas. Consequently, if the branching fork is asymmetrical, either the larger or the smaller molecules of the sample gas would be more likely to reach the connecting gas passage and, subsequently, the carrier gas passage. This would distort the measurements in the subsequent gas chromatographic analysis. In a preferred 50:50 split of the sample flow, the branching fork of the connecting gas passage from the sample gas passage is symmetrical.

As previously mentioned, the gas passages in the gas flow switching device according to the invention can be formed with great accuracy by means of micromechanical production methods, so that the geometry of the gas passages after production is very precisely known. This is advantageously exploited in that the gas flow switching device according to the invention, together with at least one chromatographic column connected thereto, includes the device for setting different pressures, wherein the device has electronic pressure regulators. The set point values of these pressure regulators are calculated and set based on geometric data of the gas passages and the separation column. In addition, these set point values are calculated and set as a function of the gas flow parameters and as a function of the temperature and the desired flow rate in the separation column. This eliminates the previously required basic pressure calibration by means of adjustable needle valves.

Since, as a rule, the inner diameter of the separation column is not exactly known due to manufacturing tolerances and due to the coating of the column with a liquid separation phase, the gas flow switching device is preferably operated with a test gas or sample gas, when the calculated set point values are set at the pressure regulators. Therein, the transit time (retention time) of the sample gas through the separation column is measured and, based thereon, the average inside diameter of the column is calculated. The sample gas is e.g. air, which does not interact with the separation phase of the column. Based on the thus determined average inner diameter of the separation column, the set point values for the pressure regulators are then recalculated and reset.

BRIEF DESCRIPTION OF THE DRAWINGS

The invention and further advantageous refinements of the invention according to the features of the dependent claims are explained in more detail below with the aid of diagrammatic, exemplary embodiments in the drawings, in which:

DETAILED DESCRIPTION OF THE PREFERRED EMBODIMENTS

Figure 1:
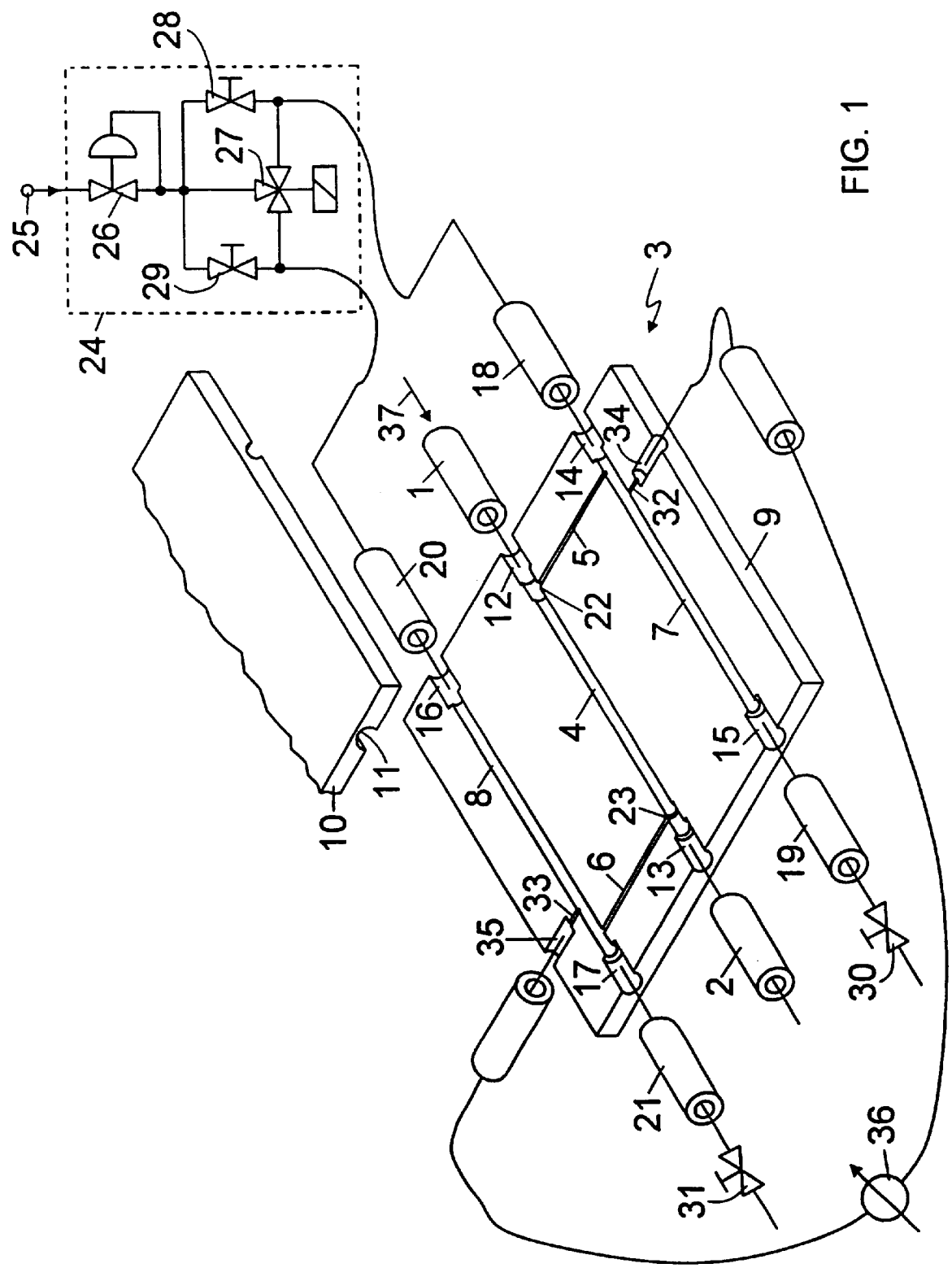
FIG. 1 shows a first embodiment of the gas flow switching device according to the invention for switching sample and carrier gas flows between two chromatographic separation columns.

FIG. 1 shows two, only partly depicted chromatographic capillary separation columns 1 and 2, which are connected to a gas flow switching device 3. The gas flow switching device 3 is configured either to direct a gas sample exiting from the one separation column, e.g., separation column 1, to the other separation column 2, or to prevent the gas sample from entering into the other separation column 2 and to divert it. To this end, the two separation columns 1 and 2 are connected with one another via a main gas passage 4, which communicates with two auxiliary gas passages 7 and 8 via two connecting gas passages 5 and 6.

To form the gas passages 4 to 8, two plates 9 and 10, which are positioned on top of one another and joined together, have congruent channels 11 with respective semicircular cross sections. These channels 11 are formed on those sides of the plates 9 and 10 that face one another. The channels 11 form the gas passages 4 to 8 and, at their lateral exit points from the plates 9 and 10, connecting points 12 to 17 of the gas passages 4 to 8. For clarity's sake, the two plates 9 and 10 are shown separated from one another. At the connecting points 12 to 17, the cross sections of the channels 11 are larger than the cross sections in the area of the gas passages 4 to 8 there between. These cross sections of the channel 11 at the connecting points 12 to 17 correspond to the outside cross sections of the capillary separation columns 1 and 2 and further capillaries 18 to 21. The further capillaries 18 to 21 are inserted into the connecting points 12 to 17 and bonded there. The cross sections of the areas of the gas passages 4 to 8 located immediately behind the connecting points 12 to 17 correspond approximately to the inner cross sections of the capillaries 1, 2, 18 to 21, so that no unnecessary flow impediments are created.

As shown in FIG. 1, the auxiliary gas passages 7 and 8 extend on either side of the main gas passage 4 and parallel thereto. The junction points 22 and 23 of the two connecting gas passages 5 and 6 to the main gas passage 4 are mutually offset along the main gas passage 4. Therein, the cross section of the main gas passage 4 in the area between the junction points 22 and 23 is smaller than in the areas between the junction points 22, 23 and the connecting points 12, 13 for the separation columns 1 or 2. The cross sections of the connecting gas passages 5 and 6 either correspond to the cross section of the main gas passage 4 in the area between the junction points 22 and 23 or they are smaller than the cross section of the main gas passage 4, as shown here.

At the connecting points 14 and 16, the auxiliary gas passages 7 and 8 are connected to a carrier gas source 25 via the capillaries 18 and 20 and via a device 24 for setting different pressures in the auxiliary gas passages 7 and 8. The device 24 includes a pressure regulator 26, the input of which is connected to the carrier gas source 25 and the output of which is connected to the two capillaries 18 and 20 via a controllable switching valve 27. Furthermore, respective needle valves 28 and 29 are inserted between the output of the pressure regulator 26 and the two capillaries 18 and 20.

The connecting points 15 and 17 of the auxiliary gas passages 7 and 8 can be connected to a monitoring detector or to a gas chromatographic detector, which is located downstream from the separation column 2, via capillaries 19 and 21. The monitor detector and the gas chromatographic detector are not shown. In a manner known from German Patent DE 2806 123 C2, the capillaries 19 and 21 have further needle valves 30 and 31 arranged therein.

In the depicted embodiment of the gas flow switching device according to the invention, the auxiliary gas passages 7 and 8 are each connected via respective branching gas passages 32 and 33, which have connecting points 34 and 35 for pressure measuring devices, in this case a differential pressure gauge 36.

For the following functional description it is assumed that a sample gas flow 37 is driven through the separation column 1. The pressure conditions in the auxiliary gas passages 7 and 8 are adjusted by means of the differential pressure gauge 36. This is accomplished by first setting the pressure in the pressure regulator 26 to a value above the pressure value that would be established based on the sample gas flow 37 flowing through the series-connected separation columns 1 and 2. The needle valves 28 and 29 are adjusted so as to establish a pressure drop between the auxiliary gas passages 7 and 8, which has, depending on the position of the switching valve 27, a different direction of action. If the pressure in the auxiliary gas passage 7 is greater than in the auxiliary gas passage 8, a pressure drop is created in the main gas passage 4, which acts from the connecting point 12 of the separation column 1 in the direction toward the connecting point 13 of the separation column 2. As a consequence, the sample gas flow 37 exiting from the separation column 1 flows through the main gas passage 4 and then enters the separation column 2. Since the pressure in the two auxiliary gas passages 7 and 8 is greater than in the main gas passage 4, no sample gas components can pass from the main gas passage 4 into the auxiliary gas passages 7 or 8. Instead, small amounts of the carrier gas reach the main gas passage 4 from the auxiliary gas passages 7 and 8. This does not affect the gas analysis, however, due to the neutral characteristics of the carrier gas.

If, by means of the switching valve 27, the direction of the pressure drop between the auxiliary gas passages 7 and 8 and thus the direction of the pressure drop within the main gas passage 4 between the connecting points 12 and 13 are reversed, the sample gas flow 37 exiting from the separation column 1 is diverted into the auxiliary gas passage 7 via the connecting gas passage 5. There, the sample gas flow 37 is transported by the carrier gas from the carrier gas source 25 in the direction of the capillaries 19. The separation column 2 is supplied with the carrier gas from the carrier gas source 25 via the capillaries 20, the auxiliary gas passage 8 and the connecting gas passage 6. This creates a slight backflow of carrier gas in the main gas passage 4, which, together with the sample gas flow 37 exiting from the separation column 1, reaches the connecting gas passage 5 and, from there, the auxiliary gas passage 7.

If no sample gas flow 37 is introduced into the separation column 1, the separation column I can be backflushed with the carrier gas from the carrier gas source 25. This is accomplished in that the pressure regulator 26 sets a pressure in the gas passages 4 to 8 and thus a pressure at the ends of the separation columns 1 and 2, which are inserted into the connecting points 12 and 13, that is greater than the pressures at the opposite ends of the two separation columns 1 and 2. The separation column 2 continues to be supplied with carrier gas from the carrier gas source 25 via the capillaries 20, the auxiliary gas passage 8 and the connecting passage 6.

Figure 2:
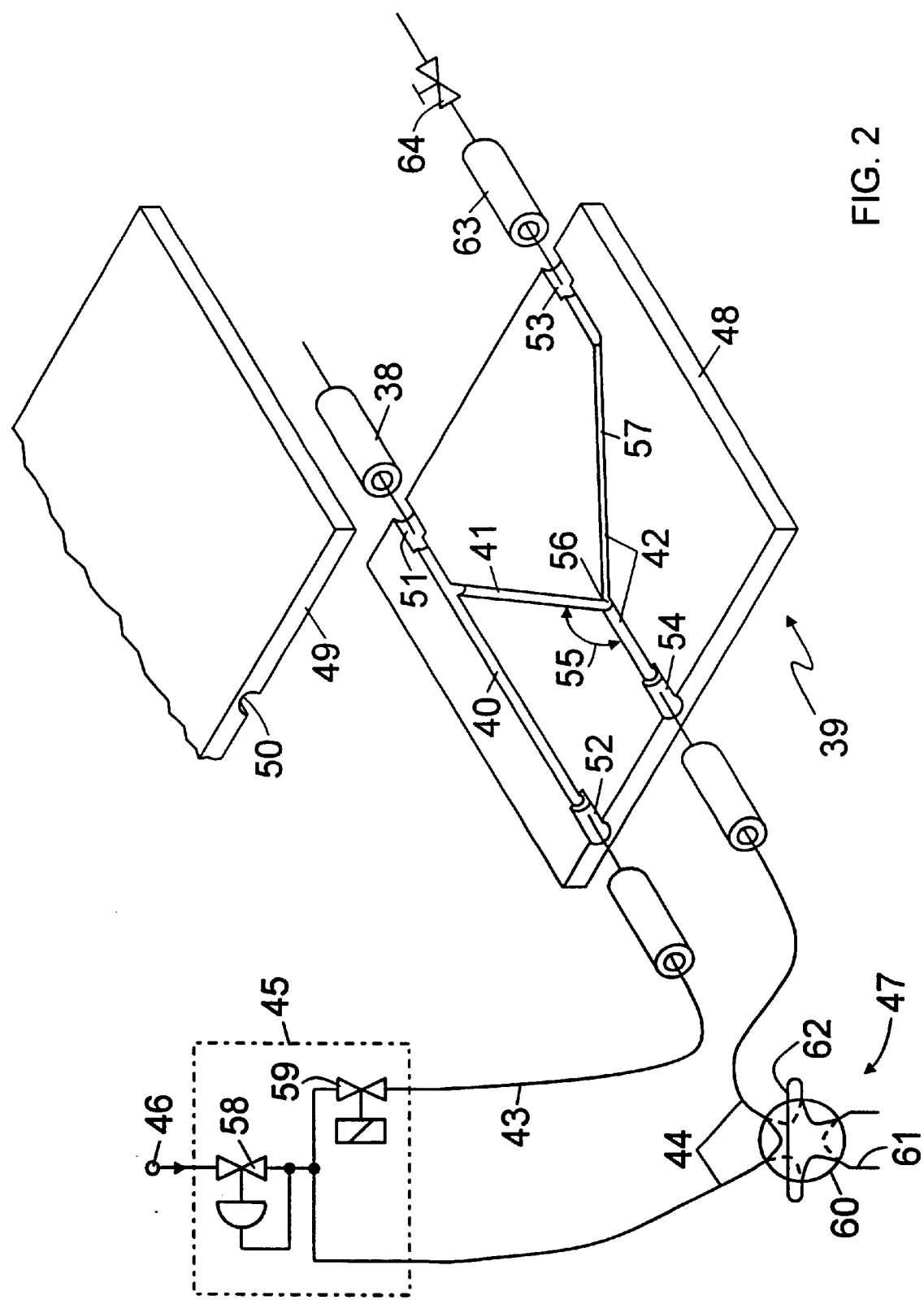
FIG. 2 shows a second embodiment of the gas flow switching device according to the invention for metering a sample gas for gas chromatographic analysis purposes.

FIG. 2 shows a portion of a chromatographic capillary column 38, which is connected to a gas flow switching device 39. The gas flow switching device 39 is configured to inject, at a predefined instant, a gas sample into a carrier gas flow flowing through the separation column 38. For this purpose, the separation column 38 is connected to one end of a carrier gas passage 40, which communicates with a sample gas passage 42 via a connecting gas passage 41. The other end of the carrier gas passage 40 and the sample gas passage 42 are connected to a carrier gas source 46 via capillaries 43 and 44 and via a device 45 for setting different pressures in the carrier gas passage 40 and the sample gas passage 42. In the course of the capillary 44 between the sample gas passage 42 and the device 45, a metering unit 47 is arranged for injecting a sample gas slug into the carrier gas flow.

To form the gas passages 40, 41 and 42, two plates 48 and 49 are positioned on top of one another and joined together. Congruent channels 50, which have respective semi-circular cross sections, are formed on those sides of the two plates that face one another. These channels form the gas passages 40, 41 and 42 and, at their lateral exit points from plates 48 and 49, connecting points 51 to 54 of the gas passages 40 to 42. For clarity's sake, the two plates 48 and 49 are shown separated from one another. At the connecting points 51 to 54, the cross sections of the channels 50 are larger than in the area of the gas passages 40 to 42 there between. These cross sections correspond to the outer cross sections of the capillary column 38 and of the capillaries 43, 44 and 63, which are inserted into the connection points 51 to 54. There, they are bonded.

As shown in FIG. 2, the connecting gas passage 41 branches off, at an obtuse angle 55, from the segment of the sample gas passage 42 coming from the connecting point 54. At a junction 56, the sample gas passage 42 continues at the same angle in another direction, so that the connecting gas passage 41 and the continuation 57 of the sample gas passage 42 form a symmetrical branching fork. The connecting gas passage 41 and the continuation 57 of the sample gas passage 42 have identical cross sections.

The device 45 for setting different pressures in the carrier gas passage 40 and in the sample gas passage 42 includes a pressure regulator 58, the input of which is connected to the carrier gas source 46 and the output of which is connected to the capillary 44 and, via a solenoid valve 59, to the capillary 43.

The metering unit 47, which is arranged in the course of capillary 44, has a metering valve 60 of known design. In its first position, which is indicated by solid lines, the metering valve guides a sample gas flow from a line 61 into a metering volume 62 and simultaneously connects the sample gas path 42 directly to the carrier gas source 46 via the device 45. In a second position, which is indicated by a dashed line, the metering volume 62 is switched directly to the capillary 44, so that the content of the metering volume 62 is transferred into the sample gas passage 42 by the carrier gas flowing through capillary 44.

The gas passages 40, 41 and 42 and the capillaries 38, 43, 44 and 63, which may have valves or restrictors installed therein, are dimensioned such that, if the solenoid valve 59 is open, the pressure in the carrier gas passage 40 is greater than that in the sample gas passage 42. As a result, no sample gas from the sample gas passage 42 can reach the carrier gas passage 40 and thus the separation column 38 via the connecting gas passage 41. If the solenoid valve 59 is closed, a reverse pressure drop results in the connecting gas passage 41 in the direction from the sample gas passage 42 to the carrier gas passage 40. Consequently, the sample gas injected into the sample gas passage 42 via the metering unit 47 is diverted from the sample gas passage 42 into the connecting gas passage 41. From there, the sample gas reaches the separation column 38 via the carrier gas passage 40. A valve 64 in the capillary 63 is used to adjust the dividing ratio of the sample gas flow to 50:50. The symmetrical embodiment of the connecting gas passage 41 and of the continuation 57 of the sample gas passage 42 at the point of the fork 56 prevents any discrimination of the differently sized gas molecules when a portion of the sample gas is diverted from the sample gas passage 42 into the connecting gas passage 41. An asymmetrical embodiment of the branching fork is also possible. In this case, the ratio of the cross sections of the connecting passage 41 and the continuation 57 of the sample gas passage 42 corresponds to the dividing ratio of the sample gas flow.

A preferred embodiment of forming the channels 11, 50 in the plates 9, 10 and 48, 49, respectively, will now be described in greater detail with reference to FIGS. 3 to 18.

Figure 3:
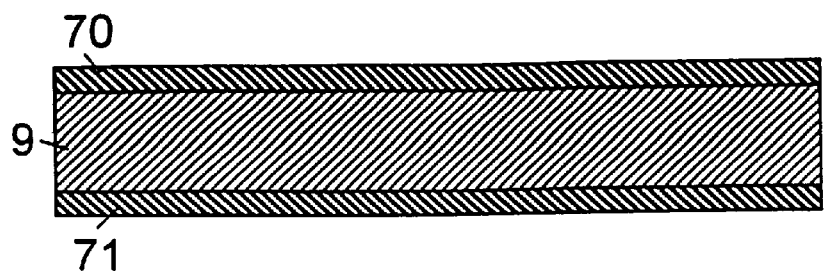
FIGS. 3 to 18 show a preferred embodiment of forming gas passages in the gas flow switching device according to the invention in several successive manufacturing steps.

FIG. 3, by way of example, shows a longitudinal section through plate 9, which extends along the main gas passage 4 to be formed in the plate 9. The plate 9 is made of monocrystalline silicon, which on its top and bottom side is provided with a silicon carbide layer 70 and 71, respectively.

Figure 4:
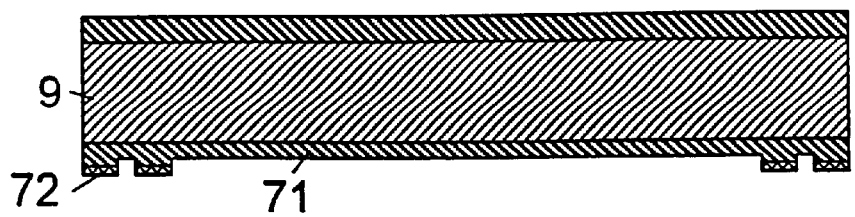

In a next step, which is illustrated in FIG. 4, saw markings are defined on the underside of the plate 9 by means of an etching mask 72 and by means of etching the silicone carbide layer 71 at points that are not covered by the etching mask 72.

Figure 5:
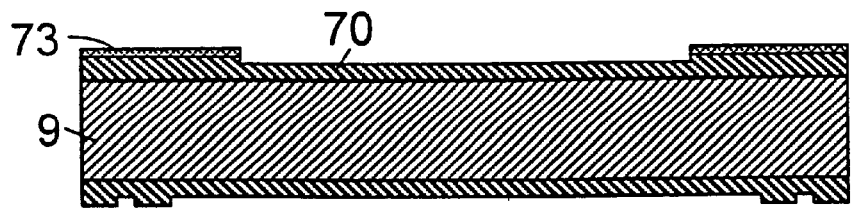
Figure 6:
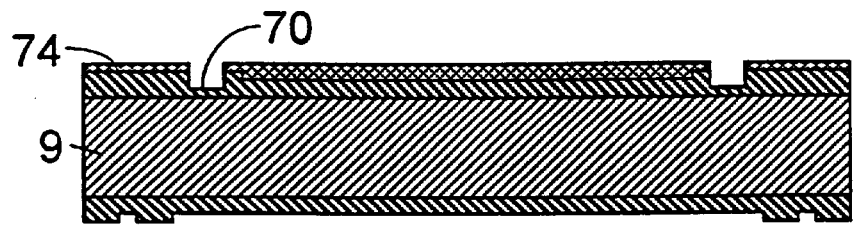

As shown in FIG. 5, by means of an etching mask 73 and by subsequent etching along a strip, which extends in the area between the junction points 22 and 23 of the main gas passage 4 to be formed, the thickness of the silicon carbide layer 70 on the upper side of the plate 9 is subsequently reduced by about one-third. FIG. 6 shows how, by means of a mask 74 and by subsequent etching of the silicon carbide layer 70, the thickness of the silicon carbide layer 70 on the upper side of the plate 9 is reduced in two narrow strips by about two thirds. These strips extend along the main gas passage 4 in the areas between the junction point 22 and the connecting point 12 as well as between the junction point 23 and the connecting point 13.

Figure 7:
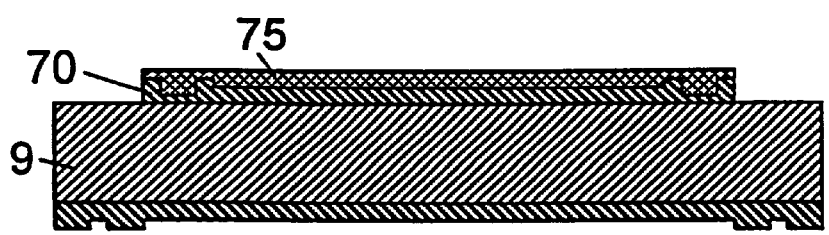

In a next process step shown in FIG. 7, the upper silicon carbide layer 70 is covered by a mask 75 with the exception of narrow strips in the areas of the connecting points 12 and 13 of the main gas passage 4 to be formed. Subsequently, the monocrystalline silicon of the plate 9 is exposed by etching away the silicon carbide 70 in the areas where it is not covered.

Figure 8:
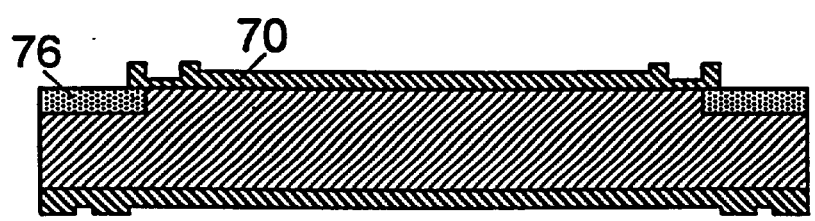

At the exposed locations, the monocrystalline silicon is then converted into porous silicon 76 up to a depth of 80 $\mu$m, as shown in FIG. 8. This conversion takes place in an isotropic etching process. Starting from the narrow strips in which the monocrystalline silicon is not covered, the isotropic etching process advances under the silicon carbide layer 70 in horizontal direction to the same degree as it progresses in depth. Thus, the areas with the porous silicon have the shape of a respective half cylinder.

Figure 9:
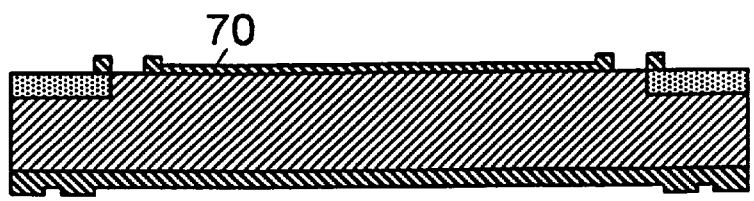

By thinning the upper silicon carbide layer 70, as shown in FIG. 9, the monocrystalline silicon is exposed in the area of the main gas passage 4 between the connecting point 12 and the junction point 22 and in the area between the connecting point 13 and the junction point 23. These areas were defined in the process step according to FIG. 6.

Figure 10:
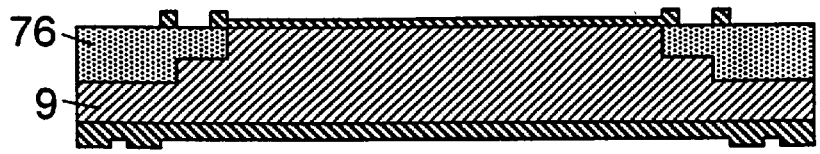

As shown in FIG. 10, the monocrystalline silicon of the plate 9 is subsequently converted into the porous silicon 76 up to a width and depth of 145 $\mu$m along the narrow strips that are not covered by the remaining silicon carbide layer 70. The areas that were previously converted into the porous silicon 76 in the process step according to FIG. 8 are further widened and deepened to 225 $\mu$m.

Figure 11:

According to FIG. 11, by further thinning the silicon carbide layer 70, the monocrystalline silicon is exposed in the area of the main gas passage 4 between the junction points 22 and 23, which was defined in the process step according to FIG. 5.

Figure 12:
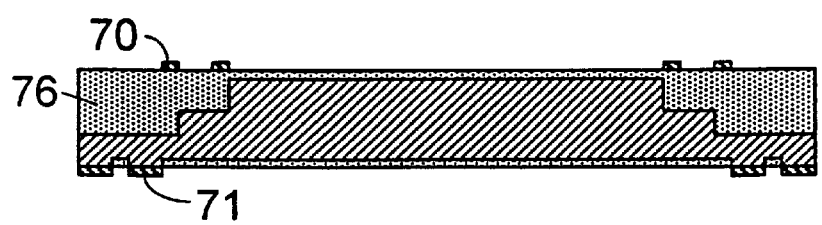

According to FIG. 12, the exposed silicon is converted into the porous silicon 76 up to a width and depth of 15 $\mu$m. The areas previously converted into the porous silicon are further widened and deepened by this amount.

Figure 13:

The remaining parts of the silicon carbide layers 70 and 71 are then removed, as shown in FIG. 13.

Figure 14:
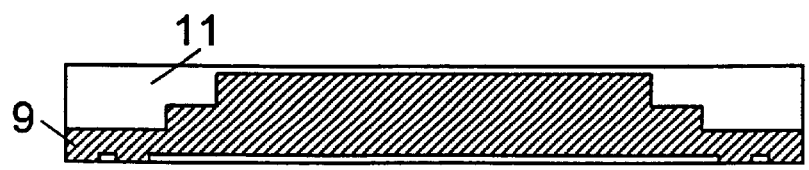

In a next process step, which is illustrated in FIG. 14, the areas in the plate 9 that were converted to the porous silicon 76 are etched away to create the channel 11 in the plate 9, wherein the channel 11 has differently sized semicircular cross sections. In the area of the subsequent connecting points 12 and 13, the semicircular cross sections have an inner radius of 240 µm. In the area between the connecting point 12 and the junction point 22 as well as in the area between the connecting point 13 and the junction point 23, the semicircular cross sections have an inner radius of 160 µm. Finally, in the area between the subsequent junction points 22 and 23, the semicircular cross sections have an inner radius of 15 µm.

Figure 15:
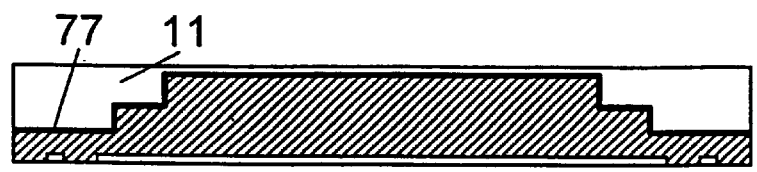

According to FIG. 15, the channel 11 is lined with a silicon dioxide layer 77.

Figure 16:
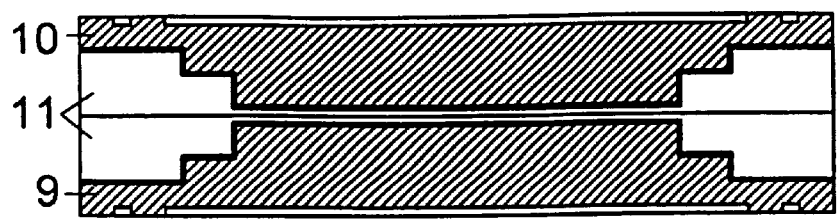

FIG. 16 shows the plate 9 after the process step indicated in FIG. 15, together with the plate 10, which is produced by means of the same process. The plates 9 and 10 are joined and adjusted so that the sides that include the channels 11 are facing one another.

Figure 17:
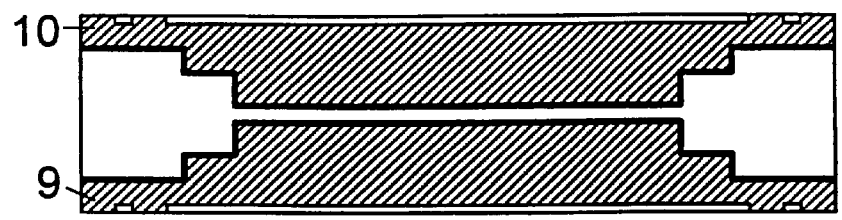

As shown in FIG. 17, the joined plates 9 and 10 are tempered at 1000° C. to connect them to one unit, which includes the gas passages formed therein such as, as illustrated here, the main gas passage 4. The connecting points 12 and 13 of the main gas passage 4 have a respective diameter of 480 µm. The areas between the connecting point 12 and the junction point 22 and between the connecting point 13 and the junction point 23 have a respective diameter of 320 µm. Finally, the areas between the junction points 22 and 23 have a respective diameter of 30 µm.

Figure 18:
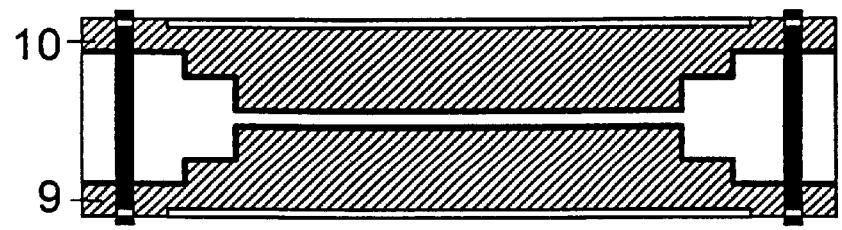

In a last process step, which is illustrated in FIG. 18, the two joined plates 9 and 10 are sawed at the saw marks, which were defined in the process step illustrated in FIG. 4.

Figure 19:
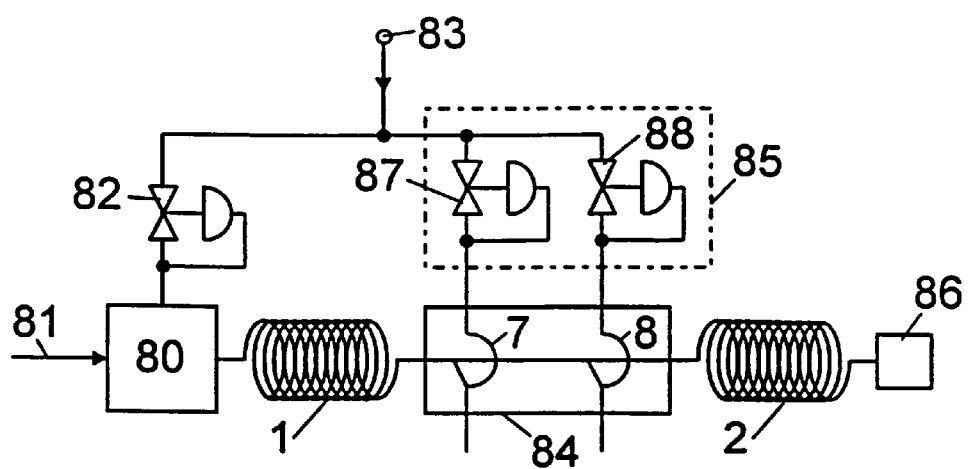
FIG. 19 is a block diagram of an embodiment of the gas flow switching device according to the invention including a device for setting different pressures, which has electronic pressure regulators.

FIG. 19 shows a block diagram of the preferred embodiment of the gas flow switching device according to the invention depicted in FIG. 1. On one side, the separation column 1 is connected to an injection unit 80, from which a gas sample 81 that is to be analyzed is guided through the separation column 1 by means of a carrier gas. To this end, the injection unit 80 is connected with a carrier gas source 83 via an electronic pressure regulator 82. At its other end, the separation column 1 is connected to a unit 84, which includes the plates 9 and 10 depicted in FIG. 1, together with the gas passages 4 to 8 formed therein. The auxiliary gas passages 7 and 8 of the unit 84 are connected to the carrier gas source 83 via a device 85 for setting different pressures in the auxiliary gas passages 7 and 8. Furthermore, the separation column 2, together with a downstream detector 86, is connected to unit 84.

In the embodiment shown here, the device 85 includes two electronic pressure regulators 87 and 88. The pressure regulator 87 connects the auxiliary gas passage 7 to the carrier gas source 83 and the pressure regulator 88 connects the auxiliary gas passage 8 to the carrier gas source 83. Due to the highly precise manufacturing data of the gas passages 4 to 8 in the unit 84, the pressures in the auxiliary gas passages 7 and 8 can be adjusted via the set points of the pressure regulators 87 and 88 without the need for calibration. To this end, all flows and pressures are calculated based on the known geometrical data of the gas passages 4 to 8 and based on the geometries of the separation columns 1 and 2. Therein, the appropriate flow rates in the separation columns 1 and 2 as a function of the gas type and of the operating temperature are taken into account. Furthermore, the compressibility of the gas is taken into account too. The calculated pressures are supplied as set point values to the pressure regulators 82, 87 and 88.

In a next step, a sample gas, e.g., air, which practically does not interact with the separation phases of the separation columns 1 and 2, is guided through the separation columns 1 and 2 via the injection device 80. The transit time of the sample gas through the separation columns 1 and 2 is measured, and from the measured transit time the average inner diameter of the separation columns 1 and 2 is calculated. By means of the average inner diameters of the separation columns 1 and 2 thus determined, the set point values for the pressure regulators 82, 87 and 88 are recalculated and finally set, so that the gas flow switching device is thereby calibrated. This eliminates a time-consuming calibration of needle valves for adjusting the pressure.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A gas flow switching device for switching gas flows between gas sources and gas sinks, comprising:
    two plates, which are positioned on top of one another and joined together, comprising congruent channels on sides of the two plates that face each other, wherein the congruent channels have respective semicircular cross sections, wherein the congruent channels form gas passages that communicate with each other, and wherein the congruent channels form connecting points for the gas sources and the gas sinks at points at which the congruent channels exit the two plates; and
    a device for setting different pressures at predefined ones of the connecting points.

2. The gas flow switching device of claim 1, wherein the respective semicircular cross sections at the connecting points are larger than the respective semicircular cross sections of the gas passages between the connecting points; and wherein capillaries that lead to the gas sources and to the gas sinks are inserted in the connecting points.

3. The gas flow switching device of claim 1, wherein the two plates comprise monocrystalline silicon, into which the congruent channels are formed by isotropic etching.

4. The gas flow switching device of claim 3, wherein, in the area of the congruent channels, the monocrystalline silicon is converted into porous silicon and subsequently removed by etching.

5. The gas flow switching device of claim 3, wherein the congruent channels are lined with a silicon dioxide layer.

6. The gas flow switching device of claim 1,
    wherein, for switching sample gas flows and carrier gas flows between two chromatographic separation columns, the congruent channels in the two plates form a main gas passage, two auxiliary gas passages, and two connecting gas passages;
    wherein a respective one of the two auxiliary gas passages extends along one side of the main gas passage;
    wherein the respective one of the two auxiliary gas passages is connected with the main gas passage via a respective one of the two connecting gas passages;
    wherein junction points of the two connecting gas passages into the main gas passage are arranged mutually offset along the main gas passage;
    wherein cross sections of the two connection gas passages are smaller than a cross section of the main gas passage and than cross sections of the two auxiliary gas passages;

wherein the cross section of the main gas passage in an area between the junction points of the two connecting gas passages is smaller than the cross section of the main gas passage outside the area;

wherein the main gas passage is series-connected between the two separation columns; and wherein the two auxiliary gas passages are, on one side, connected to a carrier gas source via the device for setting different pressures.

7. The gas flow switching device of claim 6, wherein the respective one of the two auxiliary gas passages is connected to a respective connecting point for a pressure measuring device via a respective branching gas passage.

8. The gas flow switching device of claim 1, wherein, for metering a sample gas, the congruent channels in the two plates form a carrier gas passage, a sample gas passage, and a connecting gas passage between the carrier gas passage and the sample gas passage;

wherein, at a branching point of the connecting gas passage from the sample gas passage, a ratio of a cross section of the connecting gas passage and a continuation of the sample gas passage corresponds to a predefined dividing ratio of the sample gas passage;

wherein the carrier gas passage and the sample gas passage are, on one side, connected to a carrier gas source via the device for setting different pressures; and wherein a metering device for injecting a sample gas slug into the carrier gas passage is arranged between the carrier gas source and the sample gas passage.

9. The gas flow switching device of claim 8, wherein, at the dividing ratio of the sample gas passage of 50:50, the branching point of the connecting gas passage from the sample gas passage is formed as symmetrical fork.

10. The gas flow switching device of claim 1, wherein the sample gas is metered for gas chromatographic analysis purposes.

11. The gas flow switching device of claim 1, further comprising:

at least one chromatographic separation column connected thereto, wherein the device for setting different pressures comprises electronic pressure regulators, whose set point values are calculated and set based on geometric data of the gas passages and the separation columns and as a function of parameters of a flowing gas, a temperature, and a desired flow rate within the separation columns.

12. The gas flow switching device of claim 11, wherein the gas flow switching device, with the calculated set point values being set, is operated by a sample gas, which does not interact with a separation phase of the separation columns;

wherein a transit time of the sample gas through the separation columns is measured;

wherein an average inner diameter of the separation columns is calculated based on the transmit time of the sample gas; and wherein the set point values for the pressure regulators are recalculated based on the calculated average inner diameter.

* * * * *